United States Patent [19]

Parg et al.

[11] Patent Number: 4,769,503
[45] Date of Patent: Sep. 6, 1988

[54] PREPARATION OF 3,4-DICHLOROBENZOTRIHALIDES

[75] Inventors: Adolf Parg, Bad Durkheim; Gerd Husslein, Ludwigshafen; Gerhard Hamprecht, Weinheim, all of Fed. Rep. of Germany

[73] Assignee: BASF Aktiengesellschaft, Ludwigshafen, Fed. Rep. of Germany

[21] Appl. No.: 645,814

[22] Filed: Aug. 30, 1984

[30] Foreign Application Priority Data

Sep. 6, 1983 [DE] Fed. Rep. of Germany ....... 3332017

[51] Int. Cl.$^4$ ............................................. C07C 17/12
[52] U.S. Cl. .................... 570/144; 570/191; 570/208; 570/210; 261/151
[58] Field of Search .............. 570/144, 191, 208, 210; 261/151

[56] References Cited

U.S. PATENT DOCUMENTS

| 4,023,958 | 5/1977 | Rohe et al. | 71/103 |
| 4,191,711 | 3/1980 | Lenthe et al. | 260/650 R |
| 4,207,180 | 6/1980 | Chang | 261/151 |
| 4,691,066 | 9/1987 | Inoue et al. | 570/144 |

FOREIGN PATENT DOCUMENTS

| 2520815 | 11/1976 | Fed. Rep. of Germany | 143/78 |
| 2632565 | 2/1978 | Fed. Rep. of Germany. | |
| 771416 | 7/1954 | United Kingdom. | |

OTHER PUBLICATIONS

Houben-Weyl "Methoden der Organischen Chemie" vol. 5/3 p. 652.

Primary Examiner—Glennon H. Hollrah
Assistant Examiner—John A. Sopp
Attorney, Agent, or Firm—Keil & Weinkauf

[57] ABSTRACT

A process for the preparation of 3,4-dichlorobenzotrihalides of the formula I

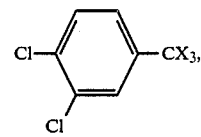

where X is fluorine or chlorine, by reacting the corresponding 4-monochlorobenzotrihalides with chlorine gas in the presence of a catalytic amount of a Lewis acid, wherein the reaction mixture is recycled by means of a pump in a circulatory apparatus with static mixers and the amount of chlorine equivalent to the conversion of the corresponding 4-monochlorobenzotrihalide is introduced at 20°–120° C.

5 Claims, 1 Drawing Sheet

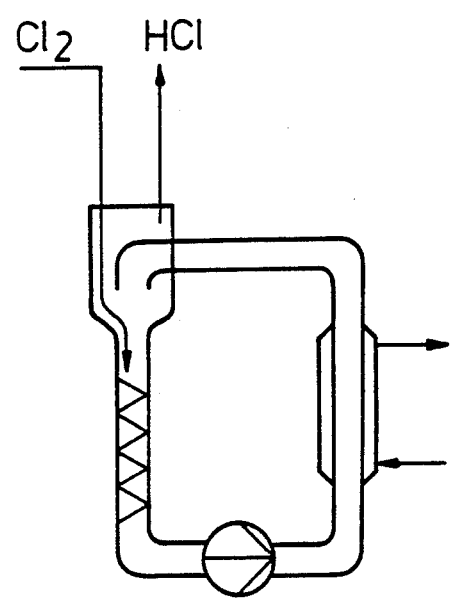

PREPARATION OF 3,4-DICHLOROBENZOTRIHALIDES

The present invention relates to a novel process for the preparation of 3,4-dichlorobenzotrihalides, starting from 4-monochlorobenzotrihalides.

Various processes for the preparation of 3,4-dichlorobenzotrihalides have been described in the literature.

According to GB-A-No. 771,416, 3,4-dichlorobenzotrichloride is obtained by treating 1,4-bis-(trichloromethyl)-2-chlorobenzene with chlorine for about 8 hours at about 250° C. A substantial disadvantage of the process is that the starting material used can only be obtained by a multi-stage process of synthesis.

Moreover, it is known from DE-A-No. 2,333,848 that 3,4-dichlorobenzotrifluoride may be prepared by chlorinating 4-chlorobenzotrifluoride in the presence of 10 mole % of iron-(III) chloride. Disadvantages of this process are on the one hand the large amount of catalyst required, which interferes with simple working-up and leads to losses in yield and, on the other hand, the simultaneous formation of more highly chlorinated products (2,4,5- and 3,4,5-trichlorobenzotrifluoride), which have to be separated off by expensive distillation.

Finally, DE-A-No. 2,644,641 describes the preparation of 3,4-dichlorobenzotrichloride starting from 4-chlorobenzotrichloride and chlorine or a chlorine donor, in the presence of iron-(III) chloride or aluminum chloride or of mixtures of these with sulfur dichloride or disulfur dichloride.

However, the following disadvantages stand in the way of industrial production using this process:

(a) The process requires a large excess of chlorine (up to 20 moles of chlorine or chlorine donor per mole of 4-chlorobenzotrichloride).

(b) Good yields are only obtained if mixtures of aluminum chloride/disulfur dichloride or iron-(III) chloride/sulfur dichloride or disulfur dichloride are employed as the catalyst.

(c) Working up is expensive because catalyst residues have to be removed.

(d) The space-time yield is poor because of the low rate of chlorination.

We have found that 3,4-dichlorobenzotrihalides of the formula I

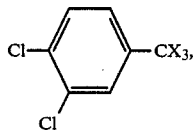

I where X is fluorine or chlorine, may be prepared advantageously and without the disadvantages mentioned at the outset, by reacting the corresponding 4-monochlorobenzotrihalides with chlorine gas in the presence of a catalytic amount of a Lewis acid, if the reaction mixture is recycled by means of a pump in a circulatory apparatus with static mixers and an equimolar amount of chlorine based on 4-monochlororobenzotrihalide, is introduced at 20°–120° C. at the rate equivalent to the conversion of the corresponding 4-monochlorobenzotrihalide Lewis acids are all substances which serve as electron pair acceptors. For the purposes of the present invention, the relevant Lewis acids are principally those conventionally employed as catalysts in the chlorination of aromatics (cf. Houben-Weyl "Methoden der Organischen Chemie" 5/3, page 652 et seq.), for example iron-(III) chloride, aluminum chloride, antimony(III) chloride, antimony(V) chloride and tin(IV) chloride. The use of iron(III) chloride proves particularly advantageous.

The amount of Lewis acid employed is from 1 to 50 millimoles, especially from 2 to 10 millimoles, per mole of 4-monochlorobenzotrihalide.

The Lewis acid is added before the reaction, the latter being preferably carried out in the absence of a solvent. Where appropriate, it is however possible to use inert solvents such as chlorohydrocarbons, eg. 1,1,2,2- or 1,1,1,2-tetrachloroethane, tetrachloroethylene, carbon tetrachloride, 1,1,1- or 1,1,2-trichloroethane or 1,2,4-trichlorobenzene.

Since the starting materials, namely 4-monochlorobenzotrifluoride or 4-monochlorobenzotrichloride, are liquid in the temperature range mentioned above, the reaction mixture obtained is either a suspension, where solid Lewis acids ($FeCl_3$ or $AlCl_3$) are used or an emulsion if liquid Lewis acids ($SbCl_5$ or $SnCl_4$) are used.

According to the invention, the reaction mixture into which chlorine gas is introduced is recycled in a circulatory apparatus. For this it is possible to use, for example, a circulatory reactor or annular reactor, equipped with a pump, advantageously a centrifugal pump, and a source of heat.

Before the chlorine gas is introduced, the reaction mixture is heated to the required temperature, a suitable range being from 20° to 120° C., and from 40° to 90° C. being preferred.

On passing the chlorine gas into the reactor, care must be taken to mix the gas thoroughly with the reaction mixture. This is achieved by the use of static mixers or mixing elements located in the circulatory apparatus.

According to the invention, the chlorine gas is passed into the reaction mixture at the rate at which chlorine is converted. It is particularly advantageous to allow maximum contact time between the chlorine gas and the 4-chlorobenzotrihalide/Lewis acid mixture. This increase in residence time of the chlorine gas in the reaction mixture is achieved, according to the invention, by circulating the reaction mixture.

The consequence is that the amount of chlorine required can be restricted to the equimolar amount, based on 4-monochlorobenzotrihalide. In some cases it can also be advantageous to introduce the chlorine gas in 10% excess.

The process is carried out batchwise but can also be performed continuously.

The reaction is carried out either under atmospheric pressure or under superatmospheric pressure, of from 2 to 100 bar.

The average reaction time can vary within a wide range and is in general from 0.5 to 12 hours.

To isolate the reaction product, dilute hydrochloric acid is added to the reaction mixture after completion of the reaction, and the organic phase is separated off, washed with water, dried and then subjected to fractional distillation. Where appropriate, the catalyst can be removed by simple filtration before the mixture is worked up.

Using the process according to the invention, the desired 3,4-dichlorobenzotrihalides are obtained isomer-free, in a yield of ≧90% and a purity of 97%.

By matching the feed of chlorine gas to the rate at which it is taken up in the reaction mixture, the reaction time of the novel process is reduced to less than half that of the conventional processes. This is assisted by increasing the residence time of the chlorine gas in the reaction mixture. As a result of the complete conversion of the added chlorine in the reaction mixture, the reaction end point is accurately determined and loss of chlorine avoided. To determine the end of the reaction, the chlorine content of the exit gas can be employed, since this rises rapidly at the end of the reaction.

Pollution of the environment by the hydrogen chloride exit gas formed in the reaction can thus be avoided by simple measures, for example by absorbing the exit gas in water, so as to form reusable hydrochloric acid.

Furthermore, the amount of catalyst can be substantially reduced compared to that employed in the conventional processes, especially when the catalyst is iron-(III) chloride. Consequently, the catalyst (Lewis acid) becomes substantially better dispersed in the reaction mixture and can be more easily removed after completion of the reaction, with only minimum losses of yield of the desired product.

The 3,4-dichlorobenzotrihalides obtainable by the novel process are valuable intermediates for the preparation of substituted diphenyl ethers which may be used as herbicides.

The Examples which follow illustrate the invention.

EXAMPLE 1

A circulatory apparatus (see the drawing) was used, equipped with static mixers, a centrifugal pump, a source of heat, a chlorine gas supply and an exit gas line for hydrogen chloride.

In this apparatus, a mixture of 1,725 g (7.5 moles) of 4-chlorobenzotrichloride and 12 g (0.075 mole) of $FeCl_3$ was heated to 70° C. and circulated. The introduction of 585 g (8.25 moles) of chlorine gas was then started. (chlorine gas was fed in at a rate such that no chlorine was detectable in the exit gas.) The reaction was complete after 5 hours. 2 liters of dilute hydrochloric acid were added to the reaction mixture and the organic phase was separated off, washed twice with 2 liters of water and dried over $CaCl_2$. Subsequent fractional distillation gave 1,824 g of 3,4-dichlorobenzotrichloride (92% of theory) (98% purity according to a gas chromatogram), of boiling point 138°–140° C. at 12 mbar.

EXAMPLE 2

The apparatus described in Example 1 was used, and in this a mixture of 1,740 g (9.67 moles) of 4-chlorobenzotrifluoride and 3.2 g (0.02 mole) of $FeCl_3$ was heated to 60° C. and circulated. The introduction of 754.3 g (10.63 moles) of chlorine gas was then commenced, similarly to the procedure in Example 1. The reaction was complete after 6 hours. The mixture was worked up as described in Example 1, and 1,996 g of 3,4-dichlorobenzotrifluoride (96% of theory), of boiling point 170°–172° C. under atmospheric pressure, were obtained.

We claim:

1. A process for the preparation of a 3,4-dichlorobenzotrihalide of formula I

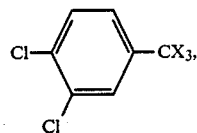

wherein X is fluorine or chlorine, which process comprises: passing chlorine gas into a recycling reaction mixture in a circulatory apparatus, said mixture containing a corresponding 4-monochlorobenzotrihalide and a catalytic amount of a Lewis acid, the temperature of said reaction mixture being from 20° to 120° C., said gas being introduced under conditions such that the gas is thoroughly mixed with the reaction mixture and at the rate at which the gas is taken up in the reaction mixture, the amount of gas passed into the reaction mixture based on the 4-monochlorobenzotrihalide being from an equimolar amount to a 10% excess molar amount, whereby said 3,4-dichlorobenzotrihalide is obtained substantially free of unwanted isomers.

2. The process of claim 1, wherein static mixing is employed.

3. The process of claim 3, wherein the reaction is carried out in the absence of a solvent.

4. The process of claim 1, wherein the temperature of the reaction mixture is from 40° to 90° C.

5. The process of claim 1, wherein said mixture of corresponding 4-monochlorobenzotrihalide and catalyst is circulated within the vessel in which reaction takes place.

* * * * *